United States Patent [19]

Coull et al.

[11] Patent Number: 5,254,476
[45] Date of Patent: Oct. 19, 1993

[54] METHOD AND SYSTEM FOR ANALYSIS OF PEPTIDES AND PROTEINS

[75] Inventors: James M. Coull, Westford; James D. Dixon, Newtonville, both of Mass.

[73] Assignee: Millipore Corporation, Bedford, Mass.

[21] Appl. No.: 893,689

[22] Filed: Jun. 5, 1992

[51] Int. Cl.$^5$ .................................. G01N 33/68
[52] U.S. Cl. .................... 436/89; 436/177; 436/161; 422/68.1; 422/70; 530/334; 530/344; 530/402; 530/412
[58] Field of Search .................. 436/86-89, 436/161, 175, 177, 178; 422/68.1, 70, 101; 530/333-345, 402, 412

[56] References Cited

U.S. PATENT DOCUMENTS

| | | | |
|---|---|---|---|
| 3,892,531 | 7/1975 | Gilbert | 23/253 R |
| 4,065,412 | 12/1977 | Dreyer | 260/8 |
| 4,603,114 | 7/1986 | Hood et al. | 436/89 |
| 4,704,256 | 11/1987 | Hood et al. | 422/68 |
| 5,039,488 | 8/1991 | Kohr | 422/68.1 |

Primary Examiner—James C. Housel
Assistant Examiner—David Redding
Attorney, Agent, or Firm—Hamilton, Brook, Smith & Reynolds

[57] ABSTRACT

A method for analysis of peptides and proteins. A peptide or protein is exposed to a coupling reagent and a buffer. The coupling reagent derivatizes the terminal amino acid residue of the peptide or protein. A cleaving-reagent is then passed across the peptide or protein in the form of a spray to cleave the derivatized terminal amino acid residue from the peptide or protein. The apparatus includes a suitable support on which a peptide or protein can be disposed. The support is disposed in a reaction chamber. Pressurized sources of a suitable coupling reagent and a buffer are connected to the reaction chamber to allow exposure of the peptide or protein on the support to the coupling reagent and the buffer. A valve is also connected to the reaction chamber. The valve includes a sliding member which causes a gas and a liquid cleaving reagent to combine, whereby a spray is formed which is conducted from the valve to the reaction chamber. The spray thereby passes across the peptide or protein on the support and cleaves the derivatized terminal residue from the peptide or protein. The terminal residue is thus liberated for isolation and identification.

10 Claims, 2 Drawing Sheets

METHOD AND SYSTEM FOR ANALYSIS OF PEPTIDES AND PROTEINS

BACKGROUND OF THE INVENTION

Determination of the sequence of amino acids in proteins and peptides is typically performed by subjecting a protein or peptide of interest to a method known as an Edman degradation. Edman degradation generally involves three chemical steps. First, an amino acid polymer, such as a protein or peptide, reacts with a suitable coupling agent, such as an isothiocyanate (e.g. phenyl isothiocyanate, PITC), at an amino terminus of the amino acid polymer in the presence of a base, such as N-methyl morpholine, to derivatize the terminal amino acid residue. The amino acid chain is then exposed to a suitable cleaving reagent (e.g. trifluoroacetic acid, TFA), whereby the terminal amino acid derivative is cleaved from the amino acid chain. The terminal amino acid derivative is then converted to a more stable derivative and identified by a suitable means, such as by chromatography (e.g., reverse-phase high pressure liquid chromatography (HPLC), thin layer chromatography or gas chromatography). Thereafter, the amino acid chain, having thus been shortened by one residue, is exposed to additional coupling and cleaving reagents to furnish a subsequent cleaved terminal amino acid derivative for identification, thereby allowing determination of the sequence of amino acids in the amino acid chain.

Edman degradation has typically been performed by passing a liquid or gaseous cleaving reagent across a substrate on which a peptide or protein has been deposited. Where a liquid cleaving reagent is employed, the peptide or protein to be sequenced is covalently attached to a substrate. A first volume of liquid reagent, including the coupling reagent in a buffered solution, is passed across the peptide or protein to derivatize the terminal amino acid residue. A second volume of liquid reagent, including the cleaving reagent, is then passed across the derivatized peptide or protein to cleave the terminal amino acid residue. The residue is then isolated and converted for identification. However, many peptides and proteins cannot be covalently attached to substrates because they do not possess the functional groups which are necessary for attachment. Another disadvantage is that the method generally requires consumption of large volumes of liquid during the coupling and cleaving steps. Often, impurities in the reagents and liquids can lower the efficiency of the process.

A second method of performing the Edman degradation includes depositing a peptide or protein onto a porous substrate by adsorption. Loss of the amino acid chain from the substrate is generally avoided by exposing the amino acid chain to coupling and cleaving reagents in the form of gases which are passed across or through the porous substrate. However, the cleaving step generates fewer cleaved derivatized residues than does the method described above which employs liquid reagents. Thus, the repetitive efficiency of the procedure is significantly diminished. Also, the utility of protocols employing gaseous-phase coupling and cleaving reagents is generally limited to the analysis of proteins and peptides that may be adsorptively bound to a substrate.

Therefore, a method is needed for determining the sequence of proteins and peptides by Edman degradation which overcome the above-mentioned problems.

SUMMARY OF THE INVENTION

The present invention relates to a method and system for liberating a terminal amino acid residue of a peptide or protein for isolation and identification of the terminal residue.

The method includes exposing a peptide or protein to a coupling reagent and a buffer, whereby the coupling reagent reacts with a terminal amino acid residue of the peptide or protein to thereby derivatize the terminal residue of the peptide or protein. The cleaving reagent is passed across the peptide or protein in the form of a spray to react with the peptide or protein and thereby cleave the terminal amino acid residue from the peptide or protein, whereby the terminal amino acid residue is liberated for isolation and identification.

The system includes means for exposing a peptide or protein to a coupling reagent and a buffer, whereby the coupling reagent reacts with a terminal amino acid residue of the peptide or protein to thereby derivatize the terminal residue of the peptide or protein. Suitable means pass the cleaving reagent across the peptide or protein in the form of a spray to react with the peptide or protein and thereby cleave the terminal amino acid residue from the peptide or protein, whereby the terminal residue is liberated for isolation and identification.

This invention has many advantages. For example, the volume of liquid employed to expose the peptide or protein to the cleaving reagent is significantly reduced, as compared to other methods, such as methods that include passing a liquid cleaving reagent across a peptide or protein which is covalently attached to a substrate. In addition, the reaction rate between the peptide or protein and the cleaving reagent and the consequent reaction yield are significantly greater than methods which employ a gaseous cleaving reagent. Further, the method of the present invention can employ peptides or proteins that are immobilized on a support either by adsorption or by covalent attachment.

DETAILED DESCRIPTION OF THE INVENTION

The features and other details of the method of the invention will now be more particularly described with reference to the accompanying drawings and pointed out in the claims. It will be understood that the particular embodiments of the invention are shown by way of illustration and not as limitations of the invention. The principle features of this invention can be employed in various embodiments without departing from the scope of the invention.

The method of the invention includes passing a cleaving-reagent spray across a peptide or protein deposited on a support to thereby cleave a derivatized amino acid terminal residue, formed by exposing the peptide or protein to a coupling agent, from the peptide or protein. Repeating the method cleaves a second derivatized residue. Identification of the sequentially cleaved terminal residues enable identification of the sequence of amino acid residues in the peptide or protein.

The peptide or protein to be sequenced can be immobilized onto a support using known immobilization methodologies. For example, the peptide or protein can be covalently attached to the support by a suitable method, such as is described in Coull et al., Anal. Biochem., 194:110–120 (1991), the teachings of which are incorporated herein by reference. Alternatively, the sample can be adsorbed onto the support by a suitable method, such as is described in Matsudaira, J. Biol. Chem., 262:1035–1038 (1987), the teachings of which are incorporated herein by reference. Still another method of depositing the peptide or protein on a support is by entrapment, such as is described in U.S. Pat. No. 5,071,909, the teachings of which are incorporated herein by reference. As stated in U.S. Pat. No. 5,071,909, entrapment can be employed in conjunction with either covalent or adsorptive attachment of peptides or proteins to the support.

Suitable supports for use with the method of the invention comprise materials which cannot be significantly degraded, either physically or chemically, by the reagents and/or conditions employed by this invention. Preferably, the support is porous to allow flow of reagents and derivatives therethrough. Suitable supports for covalent attachment of the peptide or protein to a support include, for example, Sequelon-AA ™ and Sequelon-DITC ™ attachment membranes, both commercially available from Millipore Corporation, etc. An example of a suitable membrane for adsorptively depositing a peptide or protein on a support is a support formed of polyvinylidine difluoride (PVDF), such as an Immobilon-P ™, Immobilon-P+ ™ and Immobilon-CD ™ blotting membranes, all of which are commercially available from Millipore Corporation, or a membrane formed of glass fiber, such as a GF/F glass fiber filter, commercially available from Whatman, Incorporated. Alternatively, the support can have other forms, such as beads, capillary tubes, etc.

Figure 1:
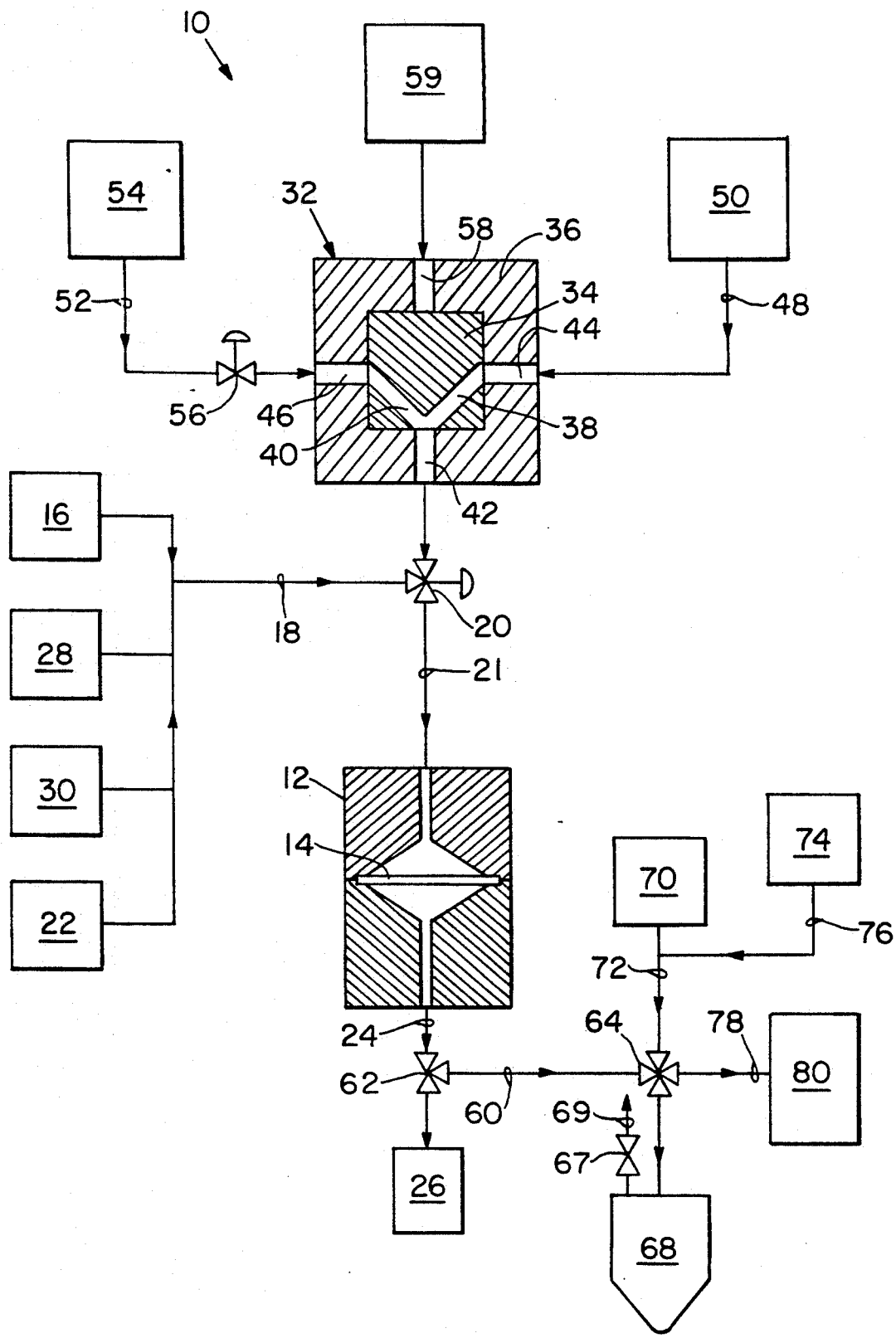
FIG. 1 is a schematic representation of one embodiment of an apparatus suitable for performing the method of the invention.

System 10, shown in FIG. 1, is a schematic representation of a system suitable for use with the method of the present invention. Preferably, system 10 is a 6625 ProSequencer ™ protein sequence analysis system (Millipore Corporation, Bedford, MA) which is controlled by a "386-based" computer control system and a PTH-Maxima software package, commercially available from Millipore Corporation. System 10 includes reaction vessel 12 having support 14 disposed within reaction vessel 12. A peptide or protein is deposited on support 14 by a suitable method, such as is described above.

System 10 is employed to perform an Edman degradation of the amino acid chain. During a preferred embodiment of the Edman degradation, the temperature in reaction vessel 12 is first adjusted to about 56° C. A suitable coupling reagent, such as phenylisothiocyanate (PITC), is directed from coupling reagent source 16 through line 18, valve 20 and line 21 to reaction vessel 12 while valve 20 is in a first position. A suitable gas for displacement of fluids from support 14, such as argon, is then directed from gas source 22 through line 18, valve 20 and reaction vessel, and from reaction vessel 12 through line 24 to container 26 to flush excess coupling reagent from reaction vessel 12.

A suitable buffer solution for use with the coupling reagent, and having a pH in the range of between about 8 and about 11, is directed from buffer source 28 through line 18, valve 20 and reaction vessel 12. An example of a suitable buffer solution is a solution of 5% N-methylmorpholine, 25% water and 70% methanol, by volume. The peptide or protein to be sequenced is then exposed to the coupling reagent and buffer solution to thereby derivatize the terminal amino acid residue of the peptide or protein. Gas is sequentially directed from gas source 22 through line 18, valve 20 and reaction vessel 12 to flush excess buffer from reaction vessel 12. Alternatively, the coupling reagent and the buffer solution can be combined prior to directing them through reaction vessel 12.

The temperature in reaction vessel 12 is then adjusted to about 45° C. A suitable wash liquid, such as a solution of 0.1% cyclohexylamine in ethyl acetate, is then directed from wash source 30 through line 18, valve 20 and reaction vessel 12 to wash residual buffer solution and unreacted coupling reagent from support 14. Valve 20 is then moved from the first position to a second position, whereby fluid communication is provided between valve 32 and reaction vessel 12.

Valve 32 includes sliding valve member 34 disposed within valve frame 36. Sliding valve member 34 defines first passageway 38 and second passageway 40. First passageway 38 and second passageway 40 converge at third passageway 42, which is defined by valve frame 36. Preferably, first passageway 38 and second passageway 40 have a substantially circular cross section and a diameter of about 0.035 inches. In a particularly preferred embodiment, first passageway 38 and second passageway 40 converge at an angle of about 90°. Valve ports 44,46, defined by valve frame 36, are disposed at first passageway 38 and second passageway 40, respectively.

Line 48, which extends between cleaving reagent source 50 and valve 32, provides fluid communication between cleaving reagent source 50 and valve port 44. Line 52 extends between gas source 54 and valve port 46. Needle valve 56 is disposed at line 52.

In one position of valve 32, cleaving reagent is directed from cleaving reagent source 50 through line 48 and into valve 32 by a suitable means, such as by pressurizing cleaving reagent source 50. In one embodiment, cleaving reagent source 50 can include a syringe. The cleaving reagent is then directed through first passageway 38 to third passageway 42. Preferably, the cleaving reagent is directed through first passageway 38 at a rate of about six microliters per minute and at a temperature which is about 25° C. An example of a suitable cleaving reagent is anhydrous trifluoroacetic acid (TFA) at a pH of less than about one. Preferably, the pH is about 0.07.

Also, while valve 32 is in the same position, gas is simultaneously directed from gas source 54 through line 52 and needle valve 56 to valve 32 by a suitable method, such as by pressurizing gas source 54. The gas is suitable for combination with the cleaving reagent to form a spray. Examples of suitable gases include inert gases, such as argon, helium, etc. Gas directed to valve 32 is conducted through second passageway 40 and combines with liquid cleaving reagent directed through first passageway 38. Preferably, needle valve 56 is adjusted to cause the gas to be discharged from gas source 54 at a rate at about eleven microliters per minute at a temperature of about 25° C. The gas at gas source 54 has a pressure of about twenty-nine psig as it is discharged from gas source 54.

Combination of the gas and the liquid cleaving reagent at valve 32 causes a formation of a cleaving reagent spray, which includes liquid droplets of the liquid cleaving reagent dispersed within a gaseous medium. The cleaving-reagent spray is subsequently directed from valve 32 through valve 20 to reaction vessel 12. The period of time over which the cleaving-reagent spray is directed to reaction vessel 12 is sufficient to cause accumulation of liquid droplets in the cleaving-reagent spray on support 14, whereby the peptide or protein on support 14 is exposed to the liquid cleaving reagent. In one embodiment, wherein the peptide or protein is adsorptively disposed onto support 14, the period of time during which the spray is directed to reaction vessel 12 is about nine minutes and fifty seconds. In another embodiment, a short pulse of spray is delivered to reaction vessel 12.

Exposure of the peptide or protein on support 14 to the liquid cleaving reagent causes the liquid cleaving reagent to react with the derivatized amino acid residue, thereby cleaving the terminal derivatized amino acid residue from the peptide or protein. More specifically, the terminal derivatized amino acid residue, in this embodiment, peptidyl phenylthiourea (PTU), cyclizes to form an anilinothiazolinone (ATZ) with concomitant cleaving of the terminal derivatized amino acid residue from the peptide or protein.

It is to be understood that valve 32 can have other positions. For example, valve 32 can have a second position, wherein a fourth passageway, not shown, defined by sliding member 32, provides fluid communication between valve port 44 and third passageway 42 for delivery of liquid cleaving reagent to reaction vessel 12. Also, valve 32 can have a third position, wherein a fifth passageway, also not shown, defined by sliding member 34, provides fluid communication between a supplemental cleaving reagent source 59 and cleaving reagent source 50 through line 61 and valve port 58, for replenishing the cleaving reagent discharged from cleaving reagent source 50.

The position of valve 20 is then moved back from the second position to the first position, whereby gas is directed from gas source 22 through valve 20, line 18, reaction vessel 12, line 60 and valve 62 to container 26. Residual spray is thereby displaced from reaction vessel 12. Wash is then directed from wash source 30 through line 18, valve 20 and through reaction vessel 12 to flush the cleaved terminal amino acid derivative from support 14 and out of reaction vessel 12. The wash and cleaved terminal derivatized amino acid residue is then conducted through line 60, valve 62, valve 64 and line 66 to conversion vessel 68. The wash is then separately removed from conversion vessel 68 by a suitable method, such as evaporation, whereby the wash is discharged to the atmosphere through valve 67 and vent 69.

A suitable conversion reagent, such as a solution of TFA in water, is directed from conversion reagent source 70 through line 72 and valve 64 to conversion vessel 68. The conversion reagent thereby combines with the cleaved terminal derivatized amino acid residue in conversion vessel 68 and reacts with the derivatized residue to form a compound, such as, in this embodiment, phenylthiohydantoin (PTH), which is more stable than the derivatized residue (ATZ). The TFA and water are then removed from conversion vessel 68 by a suitable method, such as evaporation.

A transfer liquid, such as aqueous acetyl nitrile, is then directed from transfer liquid source 74 through line 76 and 72 to conversion vessel 68 and combines with the compound in conversion vessel 68. The compound and the transfer liquid are then directed from conversion vessel 68 through valve 64 and line 78 to a suitable identification means 80 for determination of the residue cleaved from the peptide or protein in reaction vessel 12. An example of a suitable identification means is provided by the 6625 ProSequencer TM protein sequence analysis system.

The cycle of coupling, cleavage and conversion can then be repeated to identify each consecutive residue on the peptide or protein until all of the residues and their sequence have been identified.

The invention will now be further and specifically described by the following examples. All parts and percentages are by weight unless otherwise stated.

EXAMPLE I

A solution of protein A solution was prepared by dissolving purified protein A (Fermentech, Edinburgh Scotland) in deionized water. To the solution was then added $^{125}$I-radioiodinated protein A (NEN, Boston MA) to provide a solution with a final concentration of 20 pmol of protein per μL with a specific activity of 50 CPM per pmol of protein A. Disks (8 mm diameter) of PVDF membrane (Immobilon-P TM, Millipore Corp., Bedford, MA) were placed on a piece of plastic film that rested on a heat block set at 55° C. The disks were wetted with 10 μL of 50% aqueous acetonitrile. To each disk was applied 10 μL of protein A solution (200 pmol of protein, 10,000 CPM of radioactivity). The protein solution was allowed to dry onto the membrane disks over a period of 30 minutes. The disks were then removed from the heat block and stored at −20° C. prior to use.

Each membrane disk was subsequently placed in reaction vessel 12 of a Model 6625 ProSequencer TM sequencing system (Millipore Corp., Bedford, MA) depicted in FIG. 1. The instrument was operated in the manual mode whereby the operator could actuate valves and control delivery of liquids and gases as desired. Using the manual functions provided with the instrument, a spray was formed by combining argon from source 54 with trifluoroacetic acid from source 50. More specifically, the spray was formed at the junction of passageways 38 and 40 in sliding member 34 of valve 32. The spray was directed for a period of 500 seconds through passageways 42, 21 and valve 20 to reaction vessel 12 maintained at 45° C. and through the sample disk 14 and finally through passageway 24 to vessel 26. In the experiments summarized in Table 1, the gas flow rate was varied by adjusting needle valve 56 disposed between gas source 54 and valve 32. Also, the flow rate of TFA introduced into valve 32 from source 50 was varied as shown in Table 1. Disks were counted before and after exposure to the argon-TFA spray. The percent protein remaining on each disk after exposure to spray was calculated by dividing the counts remaining after exposure by the number of counts initially present on the disk.

TABLE 1

| TFA Flow Rate (μL/min) | Gas Flow Rate (mL/min) | Protein A Remaining % |
|---|---|---|
| 75 | 50 | 24.1 |

TABLE 1-continued

| TFA Flow Rate (μL/min) | Gas Flow Rate (mL/min) | Protein A Remaining % |
|---|---|---|
| 60 | 50 | 83.1 |
| 50 | 50 | 96.5 |
| 25 | 50 | 98.8 |
| 20 | 5 | 61.9 |
| 12 | 5 | 88.8 |
| 6 | 5 | 97.2 |
| 6 | 10 | 98.3 |

The results demonstrated that it was possible to form a TFA spray by control of gas and TFA flow rate so that drastic loss of sample from the support matrix in the reaction vessel did not occur. From the results in Table 1, a TFA flow rate of 6 μL/min and gas flow rate of 10 mL/min was chosen for further evaluation since greater than 98% of the protein was retained and TFA consumption was minimized. Furthermore, the temperature of the reaction vessel and duration of exposure to the spray had been chosen to be sufficient to promote cleavage of an N-terminal amino acid derivative formed by reaction of a protein N-terminal amino group with phenylisothiocyanate.

EXAMPLE II

Edman degradation cycle protocols were created using the cycle editor provided in the software of the 6625 ProSequencer ™ sequencing system. The cycle protocols contained steps that incorporated the findings from Example I. A representative cycle protocol, as shown in Table 2, was designed for use with protein/peptide samples adsorptively bound to the sample support. Step 21 of the cycle protocol in Table 2 directs the formation of the spray. Examples III–V demonstrate the utility of the cycle protocol shown in Table 2 for sequence analysis of polypeptides adsorbed to membrane supports.

TABLE 2

| | | | | | | | | |
|---|---|---|---|---|---|---|---|---|
| Coupl | 1. | Set reaction temp | [141] | Immed | | 56° C. | I | — — |
| | 2. | PITC to RC,W1 | [ 34] | 300 | μl/min | 10 sec | N | + — |
| | 3. | Gas 1 to RC,W1 | [ 73] | — | | 75 sec | I | — — |
| | 4. | BUFF to RC,W1 | [ 24] | 96 | μl/min | 12 sec | N | + — |
| | 5. | Gas 1 to RC,W1 | [ 73] | — | | 20 sec | I | — — |
| | 6. | Default RC | [ 1] | — | | 881 sec | I | — — |
| | 7. | Gas 1 to RC,W1 | [ 73] | — | | 210 sec | I | — — |
| Wash1 | 8. | Set reaction temp | [141] | Immed | | 45° C. | I | — — |
| | 9. | WSH2 to RC,W1 | [ 14] | 996 | μl/min | 5.0 sec | N | — — |
| | 10. | Gas 1 to RC,W1 | [ 73] | — | | 90 sec | I | — — |
| | 11. | Begin repeat | [130] | 3 | times | — | I | — — |
| | 12. | WSH2 to RC,W1 | [ 14] | 996 | μl/min | 15 sec | N | — — |
| | 13. | Wait | [ 3] | — | | 15 sec | I | — — |
| | 14. | End repeat | [131] | — | | — | I | — — |
| | 15. | Gas 1 to RC,W1 | [ 73] | — | | 75 sec | I | — — |
| | 16. | Wait for converter | [136] | — | | — | I | — — |
| | 17. | WSH2 to RC,AC,W4 | [ 16] | 1248 | μl/min | 40 sec | N | + — |
| | 18. | Gas 1 to RC,AC,W4 | [ 75] | — | | 90 sec | I | — — |
| | 19. | Set conversion temp | [142] | Immed | | 60° C. | I | — — |
| Cleav | 20. | Set reaction temp | [141] | Immed | | 45° C. | I | — — |
| | 21. | ACID,G2 to RC,AC,W5 | [102] | 6 | μl/min | 590 sec | N | — + |
| | 22. | Wait | [ 3] | — | | 560 sec | I | — — |
| | 23. | WSH2-W2(ACID,G2-RC,AC,W5) | [106] | 1500 | μl/min | 30 sec | N | — — |
| | 24. | G1-W2(ACID,G2-RC,AC,W5) | [108] | 6 | μl/min | 60 sec | N | + — |
| | 25. | Gas 1 to RC,AC,W5 | [ 74] | — | | 180 sec | I | — — |
| | 26. | WSH2 to W2 | [ 17] | 1500 | μl/min | 30 sec | N | — — |
| | 27. | Wait | [ 3] | — | | 10 sec | I | — — |
| | 28. | WSH2 to RC,AC,W5 | [ 15] | 498 | μl/min | 8.0 sec | N | — — |
| | 29. | Begin repeat | [130] | 3 | times | — | I | — — |
| | 30. | Wait | [ 3] | — | | 10 sec | I | — — |
| | 31. | WSH2 to RC,AC,W5 | [ 15] | 498 | μl/min | 5.0 sec | N | — — |
| | 32. | End repeat | [131] | — | | — | I | — — |
| | 33. | Hand off to converter | [129] | — | | — | I | — — |
| | 34. | WSH2 to RC,W1 | [ 14] | 0 | μl/min | 1.0 sec | N | + — |
| Wash2 | 35. | Set reaction temp | [141] | Immed | | 56° C. | I | — — |
| | 36. | Gas 1 to RC,W1 | [ 73] | — | | 120 sec | I | — — |
| | 37. | Default RC | [ 1] | — | | 1.0 sec | I | — — |
| | 38. | End of reaction section | [137] | — | | — | I | — — |
| Conv | 39. | Gas 3 to AC,W5 | [ 83] | — | | 150 sec | I | — — |
| | 40. | Set conversion temp | [142] | Immed | | 80° C. | I | — — |
| | 41. | CONV to AC,W5 | [ 63] | 300 | μl/min | 20 sec | N | — — |
| | 42. | Default AC | [ 2] | — | | 1.0 sec | I | — — |
| | 43. | Gas 4 to AC,W5 | [ 87] | — | | 10 sec | I | — — |
| | 44. | TRAN to W6 | [ 70] | 600 | μl/min | 40 sec | N | — — |
| | 45. | TRAN to AC | [ 69] | 300 | μl/min | 8.0 sec | N | — — |
| | 46. | Default AC | [ 2] | — | | 12 sec | I | — — |
| | 47. | Gas 3 to AC,W5 | [ 83] | — | | 720 sec | I | — — |
| | 48. | CONV to AC,W5 | [ 63] | 0 | μl/min | 1.0 sec | N | + — |
| Flush | 49. | TRAN to AC | [ 69] | 150 | μl/min | 20 sec | N | — — |
| | 50. | Default AC | [ 2] | — | | 200 sec | I | — — |
| | 51. | TRAN to W6 | [ 70] | 150 | μl/min | 10 sec | D | — — |
| | 52. | Set Rheodyne to load | [139] | — | | — | I | — — |
| | 53. | TRAN to AC | [ 69] | 150 | μl/min | 27 sec | D | — — |
| | 54. | UNKNOWN LC inject | [138] | — | | — | I | — — |
| | 55. | Trigger LC | [135] | — | | — | I | — — |
| | 56. | Default AC | [ 2] | — | | 1.0 sec | I | — — |
| | 57. | Gas 5 to FC | [ 92] | — | | 40 sec | I | — — |
| | 58. | TRAN to W6 | [ 70] | 0 | μl/min | 1.0 sec | N | + — |

TABLE 2-continued

| | | | | | | | |
|---|---|---|---|---|---|---|---|
| 59. Default AC | [ 2] | — | 1.0 sec | I | — | — |
| 60. Index frac collector | [134] | — | — | I | — | — |

EXAMPLE III

Protein A was dissolved in deionized water to a concentration of 4 nmol/mL as determined by amino acid analysis. An 8 mm diameter disk of PVDF membrane was placed on a heat block at 55° C. and wetted with 10 μL of 50% aqueous acetonitrile. Five microliters of protein A solution was applied to the disk. The disk was allowed to dry on the heat block for 30 minutes. The disk was then placed in the reaction vessel of the sequencer and subjected to thirty cycles of Edman degradation using the cycle protocol of Example II. An argon flow rate of 10 mL/minute was used to create the TFA spray. The PTH-amino acid derivative generated during each cycle was analyzed by reverse-phase HPLC. The quantity of derivative produced each cycle was determined by comparing the chromatographic peak area to the peak area obtained from injection of a 20 pmol PTH-amino acid standard (Sigma Chem. Co., St. Louis, MO). A semi-log plot of the amount of PTH-derivative versus the cycle number was then generated. A least-squares algorithm was used to fit a line to the plot with the intercept and slope of the line equal to the initial and repetitive sequence yields, respectively. The initial yield was 17 pmol (85%) and the repetitive yield was 95.2%.

EXAMPLE IV

Oxidized insulin A chain (1.63 nmol) (Sigma Chemical Co., St. Louis, MO) was dissolved in 0.5 mL of 50% aqueous acetonitrile containing 0.1% TFA. An 8 mm disk of charge-modified PVDF membrane (Immobilon-N ™, Millipore Corp., Bedford, MA) was placed on a heat block equilibrated at 55° C. The disk was first wet with 10 μL of 50% aqueous acetonitrile. Thereafter, 7 μL of insulin solution was applied. The membrane was allowed to dry on the heat block for 30 minutes prior to being placed in the reaction vessel of the sequencer. The disk was subjected to twenty-one cycles of Edman degradation using the cycle protocol shown in Example II. An argon flow rate of 10 mL/minute used to create the TFA spray. The initial and repetitive sequence yields were determined to be 55% and 92.9%, respectively.

EXAMPLE V

Figure 2:
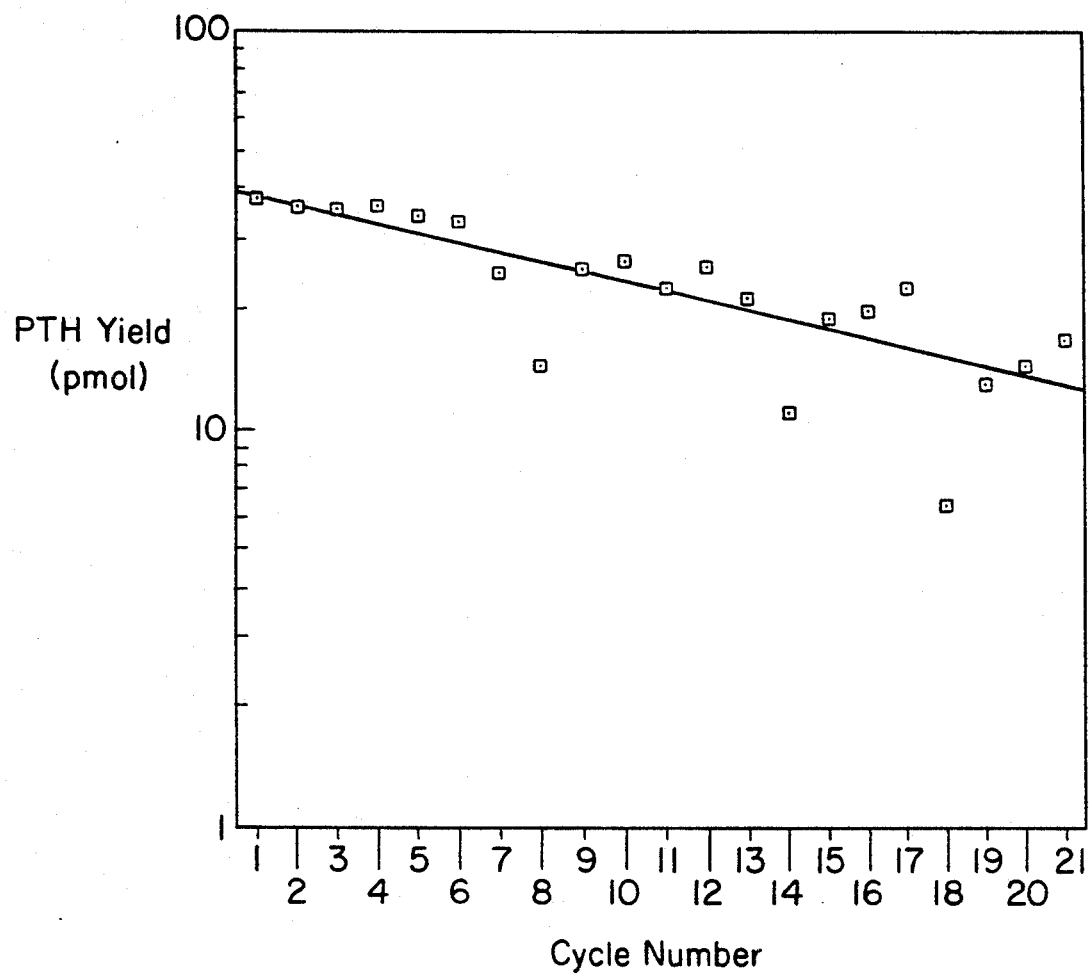
FIG. 2 is a plot of the yield resulting from a sequence analysis of yeast superoxide dismutase according to the method of the present invention.

Approximately 100 pmol of yeast superoxide dismutase was purified by gel electrophoresis and electrotransferred to a sheet of PVDF membrane using the method of Matsudaira, *J. Biol. Chem.*, 262:1035–1038 (1987). The PVDF sheet was stained with a solution of sulforhodamine to visualize the purified protein as described by J. Coull and D. Pappin, *J. Protein Chemistry*, 9:259–260). The region of membrane containing the protein was excised from the sheet and placed in the reaction vessel of the sequencer. The membrane piece was exposed to 21 cycles of Edman degradation using the cycle protocol of Example II. An argon flow rate of 10 mL/minute was used to create the TFA spray. The yield plot obtained for the sequence run is shown in FIG. 2. Each cycle corresponds to an amino acid, i.e., amino acid 1 to amino acid 21 of yeast superoxide dismutase. The initial and repetitive yields were 40 pmol (~50%) and 94.5%, respectively.

EXAMPLE VI

For proteins covalently attached to the sample support a cycle protocol was formed using the cycle editor supplied in the software of the 6625 ProSequencer ™ sequencing system. A representative Edman cycle for covalently immobilized polypeptide samples is shown in Table 3. In this protocol, a spray was created by filling passageways 44 and 42 with TFA from source 50. Gas was then introduced from source 54 through passageways 52 and 46 to combine with TFA in passageway 42. The spray was then directed through valve 20 and passageway 21 into reaction vessel 12 where it encountered sample support 14. Steps 20 and 21 of the cycle protocol listed in Table 3 direct formation of the spray.

TABLE 3

| | | | | | | P | R | S |
|---|---|---|---|---|---|---|---|---|
| Coupl | 1. Set reaction temp | [141] | Immed | 56° C. | I | — | — |
| | 2. PITC to RC,W1 | [ 34] | 300 μl/min | 10 sec | N | + | — |
| | 3. Gas 1 to RC,W1 | [ 73] | — | 75 sec | I | — | — |
| | 4. BUFF to RC,W1 | [ 24] | 96 μl/min | 12 sec | N | + | — |
| | 5. Gas 1 to RC,W1 | [ 73] | — | 20 sec | I | — | — |
| | 6. Default RC | [ 1] | — | 900 sec | I | — | — |
| Wash1 | 7. WSH1 to RC,W1 | [ 4] | 1500 μl/min | 40 sec | N | + | — |
| | 8. WSH2 to RC,W1 | [ 14] | 1500 μl/min | 40 sec | N | + | — |
| | 9. WSH1 to RC,W1 | [ 4] | 1500 μl/min | 40 sec | N | + | — |
| | 10. WSH2 to RC,W1 | [ 14] | 1500 μl/min | 40 sec | N | + | — |
| | 11. WSH1 to RC,W1 | [ 4] | 1500 μl/min | 40 sec | N | — | — |
| | 12. Default RC | [ 1] | — | 1.0 sec | I | — | — |
| | 13. Wait for converter | [136] | — | — | I | — | — |
| | 14. Gas 1 to RC,AC,W4 | [ 75] | — | 60 sec | I | — | — |
| | 15. WSH2 to RC,AC,W4 | [ 16] | 1500 μl/min | 60 sec | N | + | — |
| | 16. Gas 1 to RC,AC,W4 | [ 75] | — | 120 sec | I | — | — |
| | 17. WSH1 to RC,AC,W4 | [ 6] | 0 μl/min | 1.0 sec | N | + | — |
| | 18. Set conversion temp | [142] | Immed | 60° C. | I | — | — |
| Cleav | 19. Set reaction temp | [141] | Immed | 56° C. | I | — | — |
| | 20. ACID to RC, AC, W5 | [ 67] | 96 μl/min | 10 sec | N | — | — |
| | 21. Gas 2 to RC,AC,W5 | [ 80] | — | 5.0 sec | I | — | — |
| | 22. WSH2 to W2 | [ 17] | 0 μl/min | 1.0 sec | N | — | — |
| | 23. Wait | [ 3] | — | 139 sec | I | — | — |
| | 24. WSH2 to W2 | [ 17] | 1500 μl/min | 30 sec | N | — | — |
| | 25. Gas 1 to W2 | [ 76] | — | 30 sec | I | — | — |

TABLE 3-continued

|  | | | | | | P | R | S |
|---|---|---|---|---|---|---|---|---|
| | 26. WSH2 to W2 | [ 17] | 1500 μl/min | 30 sec | | N | — | — |
| | 27. Wait | [ 3] | — | 10 sec | | I | — | — |
| | 28. WSH2 to RC,AC,W5 | [ 15] | 498 μl/min | 8.0 sec | | N | — | — |
| | 29. Begin repeat | [130] | 3 times | — | | I | — | — |
| | 30. Wait | [ 3] | — | 10 sec | | I | — | — |
| | 31. WSH2 to RC,AC,W5 | [ 15] | 498 μl/min | 5.0 sec | | N | — | — |
| | 32. End repeat | [131] | — | — | | I | — | — |
| | 33. Hand off to converter | [129] | — | — | | I | — | — |
| | 34. ACID to RC,W1 | [ 66] | 0 μl/min | 1.0 sec | | N | + | — |
| | 35. WSH2 to RC,W1 | [ 14] | 0 μl/min | 1.0 sec | | N | + | — |
| Wash2 | 36. Gas 1 to RC,W1 | [ 73] | — | 120 sec | | I | — | — |
| | 37. Default RC | [ 1] | — | 1.0 sec | | I | — | — |
| | 38. End of reaction section | [137] | — | — | | I | — | — |
| Conv | 39. Gas 3 to AC,W5 | [ 83] | — | 150 sec | | I | — | — |
| | 40. Set conversion temp | [142] | Immed | 80° C. | | I | — | — |
| | 41. CONV to AC,W5 | [ 63] | 300 μl/min | 20 sec | | N | — | — |
| | 42. Default AC | [ 2] | — | 1.0 sec | | I | — | — |
| | 43. Gas 4 to AC,W5 | [ 87] | — | 10 sec | | I | — | — |
| | 44. TRAN to W6 | [ 70] | 600 μl/min | 40 sec | | N | — | — |
| | 45. TRAN to AC | [ 69] | 300 μl/min | 8.0 sec | | N | — | — |
| | 46. Default AC | [ 2] | — | 12 sec | | I | — | — |
| | 47. Gas 3 to AC,W5 | [ 83] | — | 720 sec | | I | — | — |
| | 48. CONV to AC,W5 | [ 63] | 0 μl/min | 1.0 sec | | N | + | — |
| Flush | 49. TRAN to AC | [ 69] | 150 μl/min | 20 sec | | N | — | — |
| | 50. Default AC | [ 2] | — | 200 sec | | I | — | — |
| | 51. TRAN to W6 | [ 70] | 150 μl/min | 10 sec | | D | — | — |
| | 52. Set Rheodyne to load | [139] | — | — | | I | — | — |
| | 53. TRAN to AC | [ 69] | 150 μl/min | 27 sec | | D | — | — |
| | 54. UNKNOWN LC inject | [138] | — | — | | I | — | — |
| | 55. Trigger LC | [135] | — | — | | I | — | — |
| | 56. Default AC | [ 2] | — | 1.0 sec | | I | — | — |
| | 57. Gas 5 to FC | [ 92] | — | 40 sec | | I | — | — |
| | 58. TRAN to W6 | [ 70] | 0 μl/min | 1.0 sec | | N | + | — |
| | 59. Default AC | [ 2] | — | 1.0 sec | | I | — | — |
| | 60. Index frac collector | [134] | — | — | | I | — | — |

EXAMPLE VII

A disk of Sequelon-DITC ™ membrane (Millipore Corp., Bedford, MA) was placed on a heat block equilibrated to 55° C. Five microliters of protein A solution as prepared in Example III was applied to the disk. The disk was then allowed to dry for five minutes. Five microliters of 2% (v/v) N-methylmorpholine (NMM) in 20% (v/v) aqueous 2-propanol was next applied to the disk. The disk was allowed to dry for five minutes and application of NMM solution was repeated. The membrane disk containing covalently bound protein A was then placed in the reaction vessel of the sequencer and exposed to 30 cycles of Edman degradation using the Edman cycle of Example VI. An argon flow rate of 10 mL/min was used to generate the TFA spray. Initial and repetitive sequence yields were determined to be 85% and 95.8%, respectively.

EXAMPLE VIII

A disk of Sequelon-AA ™ membrane (Millipore Corp., Bedford, MA) was placed on a heat block equilibrated to 55° C. Seven μL of oxidized insulin A chain solution as prepared in Example IV was then applied to the membrane disk. The disk was allowed to dry for 15 minutes. The disk was then removed from the heat block and placed on a piece of plastic film at room temperature. Five microliters of 0.1 M 4-morpholine ethanesulfonic acid, pH 5.0 containing 10 mg/mL 1-(3-dimethylaminopropyl)-3-ethylcarbodiimide hydrochloride was then applied to the disk. Twenty minutes after application of carbodiimide solution, the disk was placed in the sequencer reaction vessel and subjected to 21 cycles of Edman degradation using the Edman cycle of Example VI. An argon flow rate of 10 ml/min was used to generate the TFA spray. Initial and repetitive sequence yields of 65% and 93.6% were found, respectively.

EQUIVALENTS

Those skilled in the art will recognize, or be able to ascertain using no more than routine experimentation, many equivalents to specific embodiments of the invention described specifically herein. Such equivalents are intended to be encompassed in the scope of the following claims.

We claim:

1. A method for liberating a terminal amino acid residue of a peptide or protein for isolation and identification of the terminal residue, comprising the steps of:
   a) exposing a peptide or protein to a coupling reagent and a buffer to derivatize the terminal residue of the peptide or protein; and
   b) passing a cleaving-reagent in the form of a spray across the peptide or protein to thereby cleave the derivatized terminal residue from the peptide or protein, whereby the terminal amino acid residue is liberated for isolation and identification.

2. The method of claim 1, further including the step of depositing the peptide or protein on a support by covalent attachment of the peptide or protein to the support.

3. The method of claim 1, further including the step of depositing the peptide or protein on a support by adsorption of the peptide or protein onto the support.

4. The method of claim 3, further including the steps of:
   a) depositing a polymer onto the adsorbed peptide or protein, wherein the polymer has functional groups which can be crosslinked; and b) crosslinking the polymer to thereby produce a polymer network which entraps the peptide or protein therein, wherein the network does not interfere with subsequent chemical or enzymatic analysis of the peptide or protein.

5. The method of claim 1, wherein the cleaving-reagent spray is formed by combining a liquid cleaving-reagent stream and a gaseous stream.

6. The method of claim 5, wherein the liquid cleaving-reagent stream and the gaseous stream are combined by directing the liquid cleaving-reagent stream through a first passageway and directing the gaseous stream through a second passageway which converges with the first passageway, whereby the cleaving-reagent spray is formed at the junction of the first and second passageways and is then directed through a third passageway extending from the junction of the first and second passageways.

7. The method of claim 6, wherein the liquid cleaving reagent stream is directed through a first passageway a diameter of about 0.035 inches at a rate of above six microliters per minute, and wherein the gaseous stream is directed through a second passageway having a diameter of about 0.035 inches, and which second passageway is substantially perpendicular to the first passageway, at a rate of about eleven milliliters per minute at about atmospheric pressure and at a temperature of about 25° C.

8. The method of claim 2, wherein the peptide or protein is exposed to the coupling reagent and the buffer by sequentially passing a liquid coupling reagent and a buffer liquid across the peptide or protein deposited on the support.

9. A method for determining the amino acid sequence of a peptide or protein of interest, comprising the steps of:
   a) exposing the peptide or protein to a coupling reagent and a buffer to derivatize the terminal amino acid residue of the peptide or protein;
   b) passing a cleaving-reagent in the form of a spray across the derivatized peptide or protein to thereby cleave the derivatized terminal amino acid residue from the peptide or protein;
   c) determining the identity of the amino acid residue cleaved from the peptide or protein; and
   d) repeating steps (a) through (c) to determine the identity of the sequence of amino acids of the peptide or protein. 1

10. A system for liberating a terminal amino acid residue of a peptide or protein for isolation and identification of the terminal residue, comprising:
   a) means for depositing the peptide or protein of interest on a support; b)1 means for exposing the peptide or protein to a coupling reagent and a buffer to derivatize the terminal amino acid residue of the peptide or protein; and
   c) means for passing a cleaving-reagent in the form of a spray across the peptide or protein to thereby cleave the derivatized terminal residue from the peptide or protein, whereby the terminal amino acid residue is liberated for isolation and identification.

* * * * *